United States Patent
Broder et al.

(10) Patent No.: US 6,936,583 B2
(45) Date of Patent: Aug. 30, 2005

(54) METHOD AND COMPOSITIONS FOR ADMINISTERING TAXANES ORALLY TO HUMAN PATIENTS

(75) Inventors: Samuel Broder, Weston, FL (US); Kenneth L. Duchin, Fort Lauderdale, FL (US); Sami Selim, Irvine, CA (US)

(73) Assignee: Baker Norton Pharmaceuticals, Inc., Miami, FL (US)

( * ) Notice: Subject to any disclaimer, the term of this patent is extended or adjusted under 35 U.S.C. 154(b) by 0 days.

(21) Appl. No.: 10/794,383

(22) Filed: Mar. 5, 2004

(65) Prior Publication Data

US 2004/0171532 A1 Sep. 2, 2004

Related U.S. Application Data

(63) Continuation of application No. 10/072,398, filed on Feb. 6, 2002, now Pat. No. 6,730,698, which is a continuation of application No. 09/385,246, filed on Aug. 28, 1999, now Pat. No. 6,395,770, which is a division of application No. 08/863,513, filed on May 27, 1997, now abandoned, which is a continuation-in-part of application No. 08/733,142, filed on Oct. 16, 1996, now Pat. No. 6,245,805, which is a continuation-in-part of application No. 08/608,776, filed on Feb. 29, 1996, now Pat. No. 5,968,972.

(60) Provisional application No. 60/007,071, filed on Oct. 26, 1995.

(51) Int. Cl.$^7$ ...................... A61K 38/00; A61K 31/335
(52) U.S. Cl. ......................................... 514/11; 514/449
(58) Field of Search ................................... 514/11, 449

(56) References Cited

U.S. PATENT DOCUMENTS

| | | | |
|---|---|---|---|
| 5,112,817 A | 5/1992 | Fukazawa et al. | |
| 5,114,951 A | 5/1992 | King | |
| 5,118,493 A | 6/1992 | Kelley et al. | |
| 5,124,330 A | 6/1992 | King | |
| 5,124,338 A | 6/1992 | King | |
| 5,124,339 A | 6/1992 | King | |
| 5,166,207 A | 11/1992 | Smith | |
| 5,208,238 A | 5/1993 | King | |
| 5,300,282 A | 4/1994 | King | |
| 5,346,897 A | 9/1994 | King | |
| 5,364,843 A | 11/1994 | King | |
| 5,387,685 A | 2/1995 | Powell et al. | |
| 5,395,610 A | 3/1995 | King | |
| 5,405,843 A | 4/1995 | Fukazawa et al. | |
| 5,411,947 A * | 5/1995 | Hostetler et al. | 514/43 |
| 5,416,091 A | 5/1995 | King | |
| 5,438,072 A | 8/1995 | Bobee et al. | |
| 5,439,686 A * | 8/1995 | Desai et al. | 424/451 |
| 5,484,809 A * | 1/1996 | Hostetler et al. | 514/449 |
| 5,525,590 A | 6/1996 | Bollinger et al. | |
| 5,604,237 A * | 2/1997 | Dumaitre et al. | 514/297 |
| 5,646,176 A | 7/1997 | Golik et al. | |
| 5,665,386 A * | 9/1997 | Benet et al. | 424/451 |
| 5,670,536 A | 9/1997 | Durr et al. | |
| 5,750,561 A | 5/1998 | Bastart et al. | |
| 5,756,776 A * | 5/1998 | Bombardelli et al. | 549/510 |
| 5,776,939 A * | 7/1998 | Kroin et al. | 514/253.06 |
| 5,968,972 A * | 10/1999 | Broder et al. | 514/449 |
| 5,972,992 A | 10/1999 | Carver et al. | |
| 6,004,927 A | 12/1999 | Benet et al. | |
| 6,096,331 A | 8/2000 | Desai et al. | |
| 6,245,805 B1 * | 6/2001 | Broder et al. | 514/449 |
| 6,395,770 B1 * | 5/2002 | Broder et al. | 514/449 |
| 6,610,735 B2 * | 8/2003 | Broder et al. | 514/449 |
| 6,730,698 B2 * | 5/2004 | Broder et al. | 514/449 |

FOREIGN PATENT DOCUMENTS

| | | |
|---|---|---|
| EP | 413828 | 11/1990 |
| EP | 747385 | * 12/1996 |
| WO | WO-92/12132 | 7/1992 |
| WO | WO-95/20980 | 8/1995 |
| WO | WO-97/27855 | 8/1997 |

OTHER PUBLICATIONS

Baba et al., Cancer Chemother. Pharmacol. 36(5):361–67(1995).
Bal et al., Proc. of Am. Assoc. Pharm. Sci., Abstract PDD 7459 (Nov./1995).
Bartlett et al., J. Clin. Onc. 12(4):835–842 (1994).
Benel et al., J. Cont. Release 39:139–143 (1996).
Bissey, Euro J. Cancer 31A, Sup. 4:S1–S6 (1995).
Brock et al., Cancer Res. 55:459–462 (1995).
Chang et al., Clin. Pharm. Therap. 59:297–303 (1996).
Chiu et al., Proc. Of Am. Assoc. Pharm. Sci., Abstract PDD 7428 (Nov./1995).
Cresteil et al., Cancer Res. 54:386–392 (1994).
Duverne, et al., Antimicrobial Agents and Chemotherapy, 36(11):2462–2467 (1992).
Fisher et al., Proc. of ASCO, vol. 13:144 (1994), Abstract 369.
Fracasso et al., Proc. of ASCO 14: p. 486 (1995), Abstract 1585.
Germann et al., J. Bioenerg. Biomemb. 27:53–61 (1995).
Grant et al., Cancer Res. 54:357–361 (1994).

(Continued)

Primary Examiner—Richard L. Raymond
Assistant Examiner—Matthew L. Fedowitz
(74) Attorney, Agent, or Firm—Lerner, David, Littenberg, Krumholz & Mentlik, LLP

(57) ABSTRACT

Taxane antineoplastic agents which have heretofore exhibited poor or non-existent oral bioavailability are administered orally to human patients suffering from taxane-responsive disease conditions and made sufficiently bioavailable to achieve therapeutic blood levels. In a preferred embodiment, the taxane, preferably paclitaxel, is co-administered to the patient with an oral cyclosporin enhancing agent, preferably cyclosporin A. By one preferred method, a dose of oral enhancer is administered about 0.5–72 hours before the taxane and a second dose of the enhancer and administered immediately before, together with or immediately after the taxane. A method of treating human patients suffering from taxane-responsive disease conditions is also provided, as well as a method for providing such treatment while preventing or reducing hypersensitivity and allergic reactions without the need for pre-medication.

55 Claims, 4 Drawing Sheets

OTHER PUBLICATIONS

Harris et al., Cancer Research 54:4026/35 (1994).
Hunter, et al., Pharm Res. 10(5):743–749 (1993).
Jachez et al., J. Natl. Cancer Inst. 85(6):478–83 (1993).
Joel et al., Cancer Chemother. Pharmac. 37:125–133 (1995).
Keller, et al., Int. J. Cancer, 51:433–438 (1992).
Keogh et al., N.E. J. Med. 333(10):628–633 (1995).
Kloke et al., Klin. Wochenschr. 63:1081–1082 (1985).
Kobayashi, Proc. Ann. Meet. Am. Soc. Clin. Oncol. 15:A14889 (1996).
Kumar et al., J. of Pharmac. and Exp. Therapeutics. 268(3):1160–1165 (1994).
Lepage et al., Current Op. In Neph. And Hypert., 2:735–743 (1993).
Leu et al., Cancer Chem. Pharmac. 35(5):432–436 (1995).
Leveque et al., Anticancer Res. 15:331–336 (1995).
Loehrer, Seminars in Onc. 18(6):pp. 48–52 (1992).
Lum et al., Drug Resistance in Clin. Onc. and Hematology 9(2):319–336 (1995).
Lum et al., Clin. Onc. 10(10):1635–1642 (1992).
Montaseri et al., Pharm. Res. 12(9):S/429, Abstract PPDM 8411 (1995).
Muller, Proc. Nat. Acad. Sci. 91:13033–13037 (1994).
Pouvelle et al., J. Clin. Invest. 94:413–417 (1994).
Sato, et al., Cancer Chemother. Pharmacol. 35(4):271–277 (1995).
Scheffer et al., Nature Medicine 1(6):578–582 (1995).
Schinkel et al., J. Clin Invest. 96:1698–1705 (1995).
Schinkel et al., Cell, 77:491–502 (1994).
Slegsmund et al., J. Urol., 151:485–491 (1994).
Sikic et al., Anticancer Drug Resistance: Adv. Molec. Clin. Res., pp. 149–165 (1994).
Tsuruo, Jpn. J. Cancer Chemotherapy, 21(7):962:67, (1994) (English abstract only).
Terao, et al., J. Pharmacy & Pharmacol. 48:1083–1089(1996).
Vinceneux, et al., International Journal of Clinical Pharmacology, Therapy and Toxicology 24(3):153–158 (1986).
Wei, et al., Cancer, 15(3):161–163 (1996).
Wils et al., Biochem. Pharm. 48:1528–1530 (1994).

* cited by examiner

ORAL PACLITAXEL STUDIES IN RATS

CONCENTRATIONS OF PACLITAXEL IN HUMAN PLASMA
PATIENT #2 PROTOCOL IX 100-137
180mg

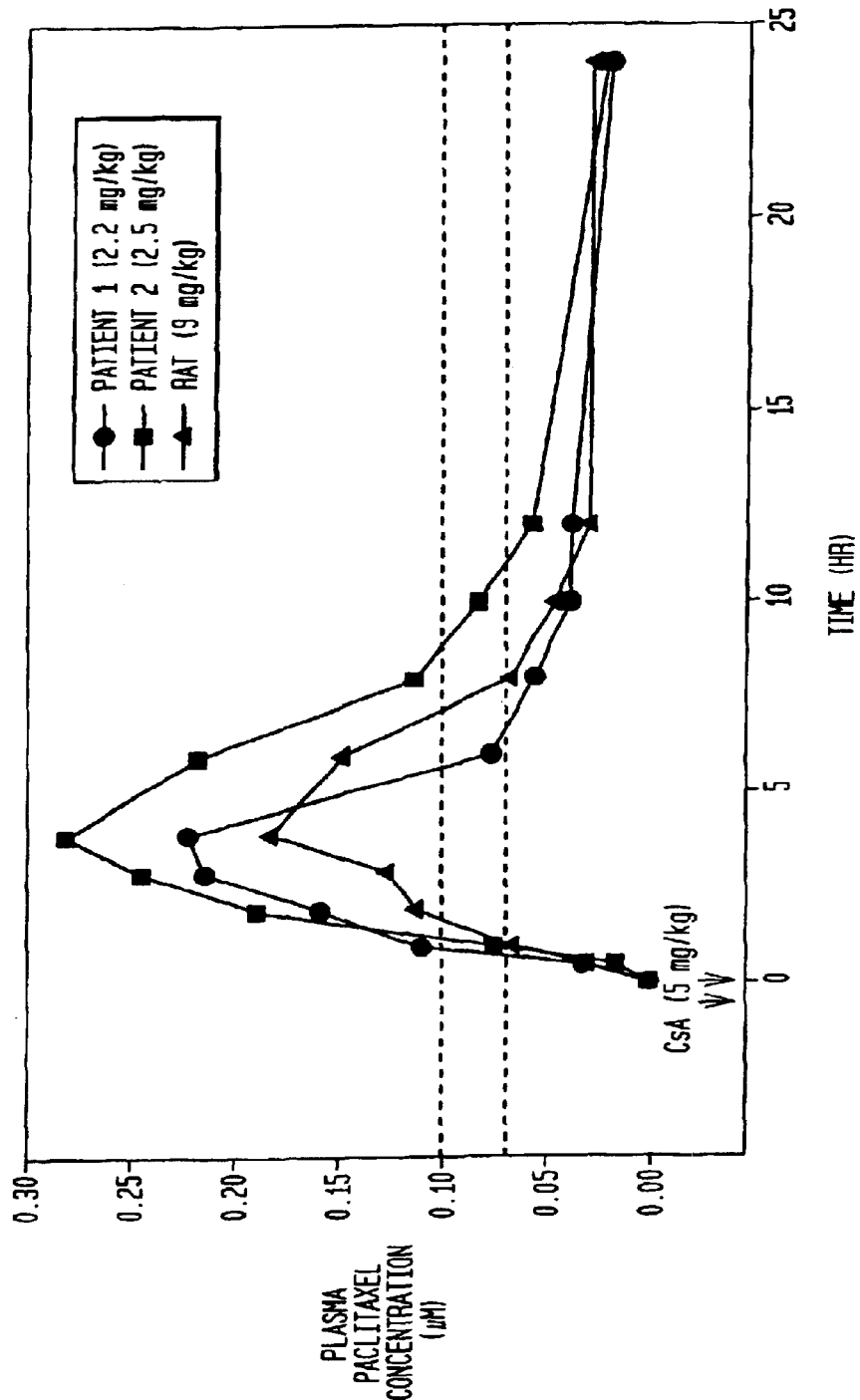

METHOD AND COMPOSITIONS FOR ADMINISTERING TAXANES ORALLY TO HUMAN PATIENTS

CROSS-REFERENCE TO RELATED APPLICATIONS

This application is a continuation of application Ser. No. 10/072,398 filed Feb. 6, 2002, now U.S. Pat. No. 6,730,689, which is a continuation of application Ser. No. 09/385,246, filed Aug. 28, 1999, now U.S. Pat. No. 6,395,770, which is a divisional of application Ser. No. 08/863,513, filed May 27, 1997, abandoned, which is a continuation-in-part of application Ser. No. 08/733,142, filed Oct. 16, 1996, now U.S. Pat. No. 6,245,805, which is a continuation-in-part of application Ser. No. 08/608,776, filed Feb. 29, 1996, now U.S. Pat. No. 5,968,972, which claims the priority of provisional application Ser. No. 60/007,071, filed Oct. 26, 1995.

REFERENCE TO DISCLOSURE DOCUMENTS

This application incorporates material included in Disclosure Document No. 377063, filed Jun. 23, 1995, No. 386504, filed Dec. 11, 1995, No. 391109, filed Feb. 7, 1996, and No. 391228, filed Feb. 7, 1996.

BACKGROUND OF THE INVENTION

The invention relates to methods and compositions for orally administering to human patients pharmaceutical agents that are poorly absorbed from the gastrointestinal tract, and to methods of treatment of patients through the oral administration of such agents. One principal aspect of the invention relates to methods and compositions for orally administering paclitaxel and related taxanes to human patients.

Many valuable pharmacologically active compounds cannot be effectively administered by the oral route to human patients because of poor or inconsistent systemic absorption from the gastrointestinal tract. All these pharmaceutical agents are, therefore, generally administered via intravenous routes, requiring intervention by a physician or other health care professional, entailing considerable discomfort and potential local trauma to the patient and even requiring administration in a hospital setting with surgical access in the case of certain IV infusions.

One of the important classes of cytotoxic agents which are not normally bioavailable when administered orally to humans are the taxanes, which include paclitaxel, its derivatives and analogs. Paclitaxel (currently marketed as TAXOL® by Bristol-Myers Squibb Oncology Division) is a natural diterpene product isolated from the Pacific yew tree (*Taxus brevifolia*). It is a member of the taxane family of terpenes. It was first isolated in 1971 by Wani et al. (*J. Am. Chem. Soc.*, 93:2325, 1971), who characterized its structure by chemical and X-ray crystallographic methods. One mechanism for its activity relates to paclitaxel's capacity to bind tubulin, thereby inhibiting cancer cell growth. Schiff et al., *Proc. Natl. Acad. Sci. USA*, 77:1561–1565 (1980); Schiff et al., *Nature*, 277:665–667 (1979); Kumar, *J. Biol. Chem.*, 256: 10435–10441 (1981).

Paclitaxel has been approved for clinical use in the treatment of refractory ovarian cancer in the United States (Markman et al., *Yale Journal of Biology and Medicine*, 64:583, 1991; McGuire et al., *Ann. Intern. Med.*, 111:273, 1989). It is effective for chemotherapy for several types of neoplasms including breast (Holmes et al., *J. Nat. Cancer Inst.*, 83:1797, 1991) and has been approved for treatment of breast cancer as well. It is a potential candidate for treatment of neoplasms in the skin (Einzig et al., *Proc. Am. Soc. Clin. Oncol.*, 20:46), lung cancer and head and neck carcinomas (Forastire et al. *Sem. Oncol.*, 20:56, 1990). The compound also shows potential for the treatment of polycystic kidney disease (Woo et al, *Nature*, 368:750, 1994) and malaria.

Paclitaxel is only slightly soluble in water and this has created significant problems in developing suitable injectable and infusion formulations useful for anticancer chemotherapy. Some formulations of paclitaxel for IV infusion have been developed utilizing CREMOPHOR EL™ (polyethoxylated castor oil) as the drug carrier because of paclitaxel's aqueous insolubility. For example, paclitaxel used in clinical testing under the aegis of the NCI has been formulated in 50% CREMOPHOR EL™ and 50% dehydrated alcohol. CREMOPHOR EL™ however, when administered intravenously, is itself toxic and produces vasodilation, labored breathing, lethargy, hypotension and death in dogs. It is also believed to be at least partially responsible for the allergic-type reactions observed during paclitaxel administration, although there is some evidence that paclitaxel may itself provoke acute reactions even in the absence of Cremophor.

In an attempt to increase paclitaxel's solubility and to develop more safe clinical formulations, studies have been directed to synthesizing paclitaxel analogs where the 2' and/or 7-position is derivatized with groups that would enhance water solubility. These efforts have yielded prodrug compounds that are more water soluble than the parent compound and that display the cytotoxic properties upon activation. One important group of such prodrugs includes the 2'-onium salts of paclitaxel and docetaxel, particularly the 2'-methylpyridinium mesylate (2'-MPM) salts.

Paclitaxel is very poorly absorbed when administered orally (less than 1%); see Eiseman et al., *Second NCI Workshop on Taxol and Taxus* (September 1992); Suffness et al. in *Taxol Science and Applications* (CRC Press 1995). Eiseman et al. indicate that paclitaxel has a bioavailability of 0% upon oral administration, and Suffness et al. report that oral dosing with paclitaxel did not seem possible since no evidence of antitumor activity was found on oral administration up to 160 mg/kg/day. Moreover, no effective method has been developed to enable the effective administration of oral paclitaxel (i.e., a method of increasing the oral bioavailability of paclitaxel) or of other oral taxanes or paclitaxel analogs such as docetaxel which exhibit antitumor activity. For this reason, paclitaxel has not until now been administered orally to human patients, and certainly not in the course of treating paclitaxel-responsive diseases.

Docetaxel (N-debenzoyl-N-tert-butoxycarbonyl-10-deacetyl paclitaxel) has become commercially available as TAXOTERE® (Rhone-Poulenc-Rorer S. A.) in parenteral form for the treatment of breast cancer. To date no reference has been made in the scientific literature to oral absorption of docetaxel in animals or patients.

It has been speculated that, in some cases, the poor or non-existent bioavailability of a drug such as paclitaxel after oral administration is a result of the activity of a multidrug transporter, a membrane-bound P-glycoprotein, which functions as an energy-dependent transport or efflux pump to decrease intracellular accumulation of drug by extruding xenobiotics from the cell. This P-glycoprotein has been identified in normal tissues of secretory endothelium, such as the biliary lining, brush border of the proximal tubule in the kidney and luminal surface of the intestine, and vascular endothelial cells lining the blood brain barrier, placenta and testis.

It is believed that the P-glycoprotein efflux pump prevents certain pharmaceutical compounds from transversing the mucosal cells of the small intestine and, therefore, from being absorbed into the systemic circulation. A number of known non-cytotoxic pharmacological agents have been shown to inhibit P-glycoprotein, including cyclosporin A (also known as cyclosporine), verapamil, tamoxifen, quinidine and phenothiazines, among others. Many of these studies were aimed at achieving greater accumulation of intravenously administered cytotoxic drugs inside tumor cells. In fact, clinical trials have been conducted to study the effects of cyclosporine on the pharmacokinetics and toxicities of paclitaxel (Fisher et al., *Proc. Am. Soc. Clin. Oncol.*, 13: 143, 1994); doxorubicin (Bartlett et al., *J. Clin. Onc.* 12:835–842, 1994); and etoposide (Lum et al., *J. Clin. Onc.* 10:1635–42, 1992), all of which are anti-cancer agents known to be subject to multidrug resistance (MDR). These trials showed that patients receiving intravenous cyclosporine prior to or together with the anti-cancer drugs had higher blood levels of those drugs, presumably through reduced body clearance, and exhibited the expected toxicity at substantially lower dosage levels. These findings tended to indicate that the concomitant administration of cyclosporine suppressed the MDR action of P-glycoprotein, enabling larger intracellular accumulations of the therapeutic agents. For a general discussion of the pharmacologic implications for the clinical use of P-glycoprotein inhibitors, see Lum et al., *Drug Resist. Clin. Onc. Hemat.*, 9: 319–336 (1995); Schinkel et al., *Eur. J. Cancer*, 31A: 1295–1298 (1995).

In the aforedescribed studies relating to the use of cyclosporine to increase the blood levels of pharmaceutical agents, the active anti-tumor agents and the cyclosporine were administered intravenously. No suggestion was made in these publications that cyclosporine could be orally administered to substantially increase the bioavailability of orally administered anti-cancer drugs and other pharmaceutical agents which are themselves poorly absorbed from the gut without producing highly toxic side effects. Indeed, in the 1995 review paper cited above, Lum et al. showed that concomitant IV administration of MDR inhibitors and chemotherapeutic agents subject to MDR increased toxicity levels and exacerbated the patients' serious side effects. Schinkel et al. briefly adverted to the fact that MDR1 and P-glycoprotein are abundant in the mucosal cells of the intestine, and that this may affect the oral bioavailability of P-glycoprotein substrate drugs, but did not suggest or imply that the oral administration of MDR suppressing agents could improve the bioavailability of the orally unavailable agents. Furthermore, like Lum et al., Schinkel et al. warned that P-glycoprotein inhibitors can dramatically increase toxicity in chemotherapy patients and should, therefore, be used cautiously.

In an earlier publication, Schinkel et al. showed that absorption of orally ingested ivermectin was increased in mice homozygous for a disruption of the MDR1 a gene in comparison with normal mice, demonstrating that P-glycoprotein played a major role in reducing the bioavailability of this agent (*Cell*, 77: 491–502, 1994). In addition, this study also showed that the penetration of vinblastine into various tissues was enhanced in the mutant mice.

None of the published studies provided any regimen for implementing the effective oral administration to humans of poorly bioavailable drugs such as paclitaxel, e.g., indicating the respective dosage ranges and timing of administration for specific target drugs and bioavailability-enhancing agents are best suited for promoting oral absorption of each target drug or class of drugs.

Methods disclosed in the art for increasing gut absorption of drugs that have until now only been administered parenterally generally focus on the use of permeation and solubility enhancers as promoting agents, or the co-administration by intraluminal perfusion in the small intestine or by the intravenous route of P-glycoprotein inhibitors, e.g., Leu et al., *Cancer Chemother. Pharmacol.*, 35: 432–436, 1995 (perfusion or IV infusion of quinidine suppresses efflux of etoposide into the lumen of the G.I. tract from the blood). But these methods suffer from numerous drawbacks. The solubility and permeability enhancing agents are often either impractical or ineffective for oral administration in the doses required and may interfere with the pharmacological activity of the target drug. Parenteral administration of P-glycoprotein inhibitors in therapeutic (or near-therapeutic) doses into humans can cause severe clinical consequences. In the case of quinidine, for example, IV administration may cause arrhythmias, peripheral vasodilation, gastrointestinal upset and the like. Most important, they do not teach how to administer any anti-tumor agents orally to human beings.

In published PCT application WO 95/20980 (published Aug. 10, 1995) Benet et al. disclose a purported method for increasing the bioavilability of orally administered hydrophobic pharmaceutical compounds. This method comprises orally administering such compounds to the patient concurrently with a bioenhancer comprising an inhibitor of a cytochrome P450 3A enzyme or an inhibitor of P-glycoprotein-mediated membrane transport. Benet et al., however, provide virtually no means for identifying which bioavailability enhancing agents will improve the availability of specific "target" pharmaceutical compounds, nor do they indicate specific dosage amounts, schedules or regimens for administration of the enhancing or target agents. In fact, although the Benet application lists dozens of potential enhancers (P450 3A inhibitors) and target drugs (P450 3A substrates), the only combination of enhancer and target agent supported by any experimental evidence in the application is ketoconazole as the enhancer and cyclosporin A as the target drug.

When describing the general characteristics of compounds which can be used as bioenhancers by reduction of P-glycoprotein transport activity, Benet et al. indicate that these are hydrophobic compounds which generally, but not necessarily, comprise two co-planar aromatic rings, a positively charged nitrogen group or a carbonyl group—a class that includes an enormous number of compounds, most of which would not provide the desired absorption enhancing activity in the case of specific target agents. Moreover, the classes of target agents disclosed by Benet et al. include the great majority of pharmaceutical agents listed in the *Physicians' Desk Reference*. These inclusion criteria are of no value to medical practitioners seeking safe, practical and effective methods of orally administering specific pharmaceutical agents.

A further deficiency with Benet et al.'s disclosure is the standard applied for determinating whether bioavailability of a drug that is poorly absorbed upon oral administration has been improved. Benet et al. indicate that any P-glycoprotein inhibiting agent which, when present in the gut at a given concentration, reduces transmembranal transport of Rhodamine 123 by P-glycoprotein in brush border membrane vesicles or P-glycoprotein containing cells by 10% or more may be considered a bioenhancing agent at that concentration and can be used in the practice of their invention. But an increase of only 10% in absorption from the gut of an otherwise not absorbable agent is inadequate to render the agent therapeutically valuable for any purpose. Indeed, under guidelines of the Federal Food and Drug Administration, two pharmaceutical formulations containing the same active ingredient, but differing in their bioavailability levels by −20%/+25%, are still considered bioequivalent because for most drugs a −20%/+25% difference in concentration of the active ingredient in the blood is not clinically significant. *Approved Drug Products with Therapeutic Equivalence Evaluations* (Dept. of HHS, 14th ed. 1994). When the FDA rules that two pharmaceutical formulations are bioequivalent, physicians and pharmacists consider them freely substitutable for one another.

In general, Benet et al. provides no teaching that could be followed by persons skilled in the medical and pharmaceutical arts to identify suitable bioenhancer/target drug combinations or to design specific treatment regimens and schedules which would render the target agents therapeutically effective upon oral administration to human patients. Benet et al. also provides no direction whatsoever regarding how paclitaxel and other taxanes might be administered orally to humans with therapeutic efficacy and acceptable toxicity.

Thus, a safe yet effective method for increasing the systemic availability upon oral administration to human patients of drugs that are currently administered only parenterally because they are not absorbed sufficiently or consistently when administered by the oral route is required, and has not been provided in the prior art.

SUMMARY OF THE INVENTION

Surprisingly, it has now been discovered and experimentally verified that the taxane class of antineoplastic agents, particularly paclitaxel, can be orally administered to human beings with substantial and therapeutic blood levels being achieved, and with no undue toxicity or adverse side effects observed even without pre-administration of medications to prevent adverse reactions.

The present invention relates in its principal aspect to the oral administration of one or a combination of taxanes to human patients suffering from disease conditions responsive to those agents. A preferred embodiment of the invention is a method of increasing the oral bioavailability in humans of taxanes, which are poorly absorbed or not absorbed at all from the gastrointestinal tract or gut, by pre-administering and/or simultaneously administering to a human subject by the oral route one or a combination of agents ("enhancing agents") effective in inhibiting cellular multi-drug resistance. If pre-administration is used, the bioavailability enhancing agent or agents must be administered in sufficient quantities and within a short enough time period before administration of the taxane whose bioavailability is to be increased (the "target drug" or "target agent") so that a sufficient level of the enhancing agent remains at the site of absorption at the time of administration of the target agent to effectively suppress the activity of the multi-drug transporter substances, metabolic enzymes and/or other factors which prevent or inhibit gut absorption of the target agent.

A second aspect or embodiment of the invention pertains to a method of treating patients suffering from taxane-responsive diseases through the oral administration of taxanes that were heretofore available by parenteral administration only. Yet another aspect or embodiment is a method of preventing or reducing hypersensitivity and allergic reactions in patients receiving taxane therapy.

BRIEF DESCRIPTION OF THE DRAWINGS

FIG. 4 is a graph reflecting a comparison of the paclitaxel plasma level curves determined over 24 hours in rats (FIG. 1) and in humans (FIGS. 2 and 3) administered oral paclitaxel after two doses of oral cyclosporin A.

DETAILED DESCRIPTION OF THE INVENTION

Figure 1:
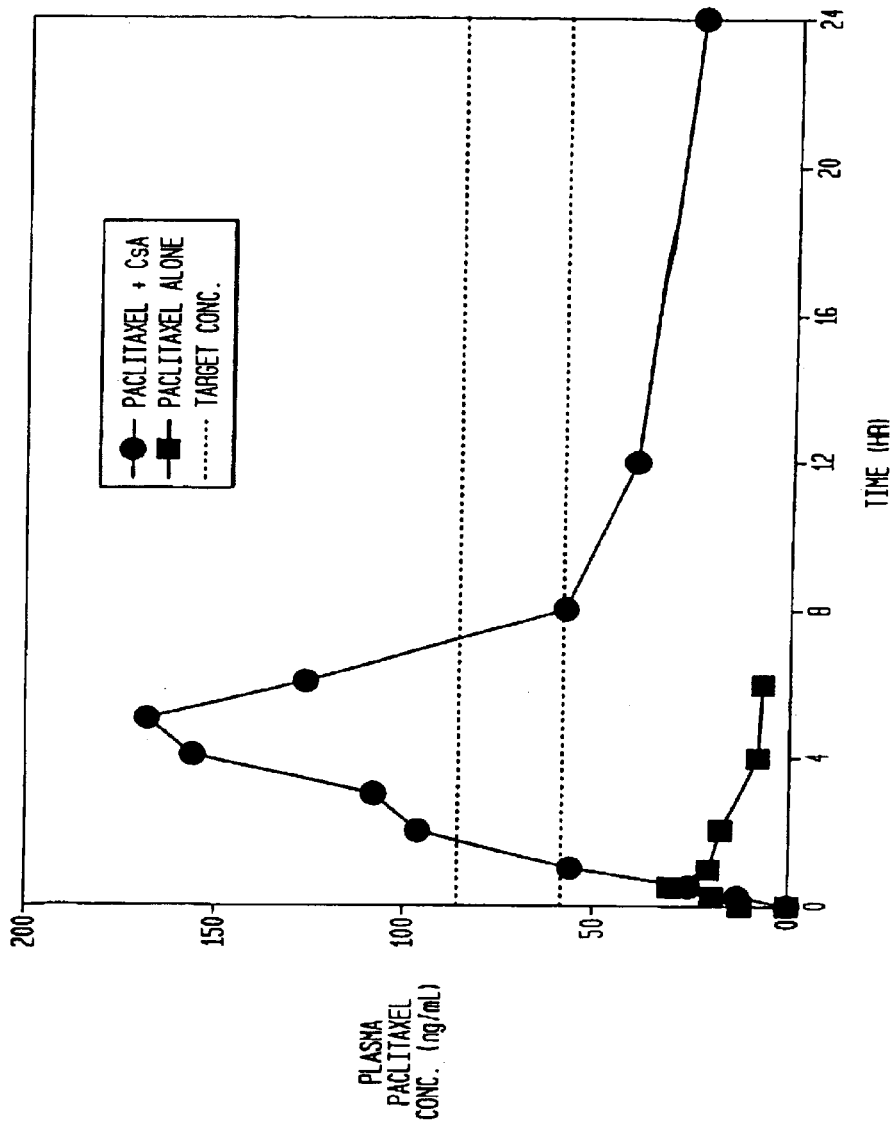
FIG. 1 is a graph reflecting the circulating levels of paclitaxel in samples taken: (a) lower curve—over a period of 6–8 hours from one group of rats administered only oral paclitaxel, and (b) upper curve—over a period of 24 hours from a second group of rats administered orally one hour prior to the co-administration of oral cyclosporin A and oral paclitaxel.

The present invention pertains in its principal aspect to the oral administration of the taxane class of antineoplastic agents, in particular paclitaxel and its derivatives, analogs and prodrugs, and the semi-synthetic paclitaxel analog docetaxel (N-debenzoyl-N-tert-butoxycarbonyl-10-deacetyl paclitaxel), to human patients suffering from taxane-responsive disease conditions. The preferred embodiments or aspects of the invention include (a) methods for oral administration of taxanes heretofore administered only parenterally with sufficient bioavailability to achieve therapeutic blood levels; (b) methods of treating human patients suffering from taxane-responsive disease conditions through the oral administration of taxanes; and (c) methods of preventing or reducing hypersensitivity and allergic reaction in patients receiving taxane therapy.

The term "bioavailability" as used herein refers to the systemic availability (i.e., blood/plasma levels) of a given amount of drug administered to a patient.

It has now been discovered that the taxanes, which have poor oral absorption profiles, can be administered orally to humans with sufficient systemic absorption and oral bioavailability achieved to exhibit plasma levels in the therapeutic range. In fact, we have actually administered the taxane paclitaxel orally to human patients suffering from cancers and have verified that therapeutic blood levels of paclitaxel were achieved in these patients over extended periods of time.

We have observed in animal studies that certain agents such as cyclosporin A, when administered orally immediately after and/or before drugs such as paclitaxel, increase absorption of the latter drugs from the gut to an unexpected and surprising degree resulting in therapeutic levels being achieved. It is not at all clear, however, that these observed results are due to the suppression of the P-glycoprotein pump.

It is emphasized that the present invention is not limited to the use of any particular oral bioavailability-enhancing agents for co-administration with an oral taxane to make the latter bioavailable to human patients. The invention resides broadly in the oral administration of taxanes to human patients, and is not restricted to any specific enhancers, dosage amounts or regimens or the utilization of particular biological mechanisms or pharmaceutical techniques to make the taxanes available for oral administration to humans.

The preferred embodiment of the method of the invention for oral administration to humans of paclitaxel, its derivatives, analogs and prodrugs, and other taxanes comprises the oral administration of an oral absorption or bioavailability enhancing agent to a human patient simultaneously with, or prior to, or both simultaneously with and prior to the oral administration to increase the quantity of absorption of the intact target agent into the bloodstream.

The orally administered enhancing agents which may be used in practicing the preferred embodiment of the invention include, but are not limited to, the following: Cyclosporins, including cyclosporins A through Z but particularly cyclosporin A (cyclosporine), cyclosporin F, cyclosporin D, dihydro cyclosporin A, dihydro cyclosporin C, acetyl cyclosporin A, PSC-833, SDZ-NIM 811[1] (both from Sandoz Pharmaceutical Corp). The structures of cyclosporins A–Z are described in Table 1 below.

[1] SDZ-NIM 811 is (Me-Ile-4)-cyclosporin, an antiviral, non-immunosuppressive cyclosporin.

The class of orally administered target therapeutic agents whose oral absorption is increased by the enhancing agents includes, but is not limited to, the following:
Paclitaxel, other taxanes, docetaxel and derivatives and prodrugs of all of the foregoing, particularly their 2'-MPM salts and other 2'-methylpyridinium salts.

synthetic and semi-synthetic analogs have also been prepared. See generally Jegorov et al., *Phytochemistry*, 38: 403–407 (1995). The present invention comprehends natural, semi-synthetic and synthetic analogs of cyclosporins.

Cyclosporins are neutral, lipophilic, cyclic undecapeptides with molecular weights of about 1200. They are used intravenously or orally as immunosuppressants, primarily for organ transplantation and certain other conditions. Cyclosporins, particularly cyclosporine (cyclosporin A), are known inhibitors of the P-glycoprotein efflux pump and other transporter pumps as well as of certain P450 degradative enzymes, but to date no effective regimens for applying this property clinically have been developed to the point of clinical and commercial feasibility or regulatory approval.

One of the surprising discoveries of the invention is that the immunosuppression observed with certain cyclosporins is not inextricably linked to improvement in oral bioavailability of therapeutic agents. Thus, cyclosporin F enhances the oral bioavailability of paclitaxel even though, according to reports in the literature, it does not display immunosuppressive activity. Stewart et al., *Transplantation Proceedings*, 20: (Supp. 3) 989–992 (1988); Granelli-Piperno et al., *Transplantation*, 46:53S–60S (1988).

TABLE 1

Cyclosporins A–Z

| Cyclosporin | Amino Acids | | | | | | | | | | |
|---|---|---|---|---|---|---|---|---|---|---|---|
| Cy- | 1 | 2 | 3 | 4 | 5 | 6 | 7 | 8 | 9 | 10 | 11 |
| CyA | Mebmt | Abu | Sar | MeLeu | Val | MeLeu | Ala | D-Ala | MeLeu | MeLeu | MeVal |
| CyB | Mebmt | Ala | Sar | MeLeu | Val | MeLeu | Ala | D-Ala | MeLeu | MeLeu | MeVal |
| CyC | Mebmt | Thr | Sar | MeLeu | Val | MeLeu | Ala | D-Ala | MeLeu | MeLeu | MeVal |
| CyD | Mebmt | Val | Sar | MeLeu | Val | MeLeu | Ala | D-Ala | MeLeu | MeLeu | MeVal |
| CyE | Mebmt | Abu | Sar | MeLeu | Val | MeLeu | Ala | D-Ala | MeLeu | MeLeu | Val |
| CyF | Desoxy-Mebmt | Abu | Sar | MeLeu | Val | MeLeu | Ala | D-Ala | MeLeu | MeLeu | MeVal |
| CyG | Mebmt | Nva | Sar | MeLeu | Val | MeLeu | Ala | D-Ala | MeLeu | MeLeu | MeVal |
| CyH | Mebmt | Abu | Sar | MeLeu | Val | MeLeu | Ala | D-Ala | MeLeu | MeLeu | D-Mev |
| CyI | Mebmt | Val | Sar | MeLeu | Val | MeLeu | Ala | D-Ala | MeLeu | Leu | MeVal |
| CyK | Desoxy-Mebmt | Val | Sar | MeLeu | Val | MeLeu | Ala | D-Ala | MeLeu | MeLeu | MeVal |
| CyL | Bmt | Abu | Sar | MeLeu | Val | MeLeu | Ala | D-Ala | MeLeu | MeLeu | MeVal |
| CyM | Mebmt | Nva | Sar | MeLeu | Val | MeLeu | Ala | D-Ala | MeLeu | MeLeu | MeVal |
| CyN | Mebmt | Nva | Sar | MeLeu | Val | MeLeu | Ala | D-Ala | MeLeu | Leu | MeVal |
| CyO | MeLeu | Nva | Sar | MeLeu | Val | MeLeu | Ala | D-Ala | MeLeu | MeLeu | MeVal |
| CyP | Bmt | Thr | Sar | MeLeu | Val | MeLeu | Ala | D-Ala | MeLeu | MeLeu | MeVal |
| CyQ | Mebmt | Abu | Sar | Val | Val | MeLeu | Ala | D-Ala | MeLeu | MeLeu | MeVal |
| CyR | Mebmt | Abu | Sar | MeLeu | Val | Leu | Ala | D-Ala | MeLeu | Leu | MeVal |
| CyS | Mebmt | Thr | Sar | Val | Val | MeLeu | Ala | D-Ala | MeLeu | MeLeu | MeVal |
| CyT | Mebmt | Abu | Sar | MeLeu | Val | MeLeu | Ala | D-Ala | MeLeu | Leu | MeVal |
| CyU | Mebmt | Abu | Sar | MeLeu | Val | Leu | Ala | D-Ala | MeLeu | MeLeu | MeVal |
| CyV | Mebmt | Abu | Sar | MeLeu | Val | MeLeu | Ala | D-Ala | MeLeu | MeLeu | MeVal |
| CyW | Mebmt | Thr | Sar | MeLeu | Val | MeLeu | Ala | D-Ala | MeLeu | MeLeu | Val |
| CyX | Mebmt | Nva | Sar | MeLeu | Val | MeLeu | Ala | D-Ala | Leu | MeLeu | MeVal |
| CyY | Mebmt | Nva | Sar | MeLeu | Val | Leu | Ala | D-Ala | MeLeu | MeLeu | MeVal |
| CyZ | MeAminooctyl acid | Abu | Sar | MeLeu | Val | MeLeu | Ala | D-Ala | MeLeu | MeLeu | MeVal |

Cyclosporins are a group of nonpolar cyclic oligopeptides (some of which have immunosuppressant activity) produced by the genus *Tolypocladium*, including, e.g., *Tolypocladium inflatum* Gams (formerly designated as *Trichoderma polysporum*), *Tolypocladium terricola* and other fungi imperfecti. The major component, cyclosporin A (cyclosporine or CsA), has been identified along with several other lesser metabolites, for example, cyclosporins B through Z, some of which exhibit substantially less immunosuppressive activity than cyclosporin A. A number of Another possible explanation for the observed increased bioavailability of paclitaxel is that there may be interaction at the level of the drug metabolizing enzymes for cyclosporine and paclitaxel. It is known that both agents are highly metabolized by the cytochrome P-450 system (e.g., P-450 3A), which is concentrated in the liver as well as the small intestine. It is conceivable that cyclosporine which was administered first may have inhibited these enzymes so that paclitaxel, which is non-polar and lipophilic, could be absorbed. In the absence of this local inhibition, paclitaxel would be metabolized to more polar metabolites which would not transverse the mucosal cells.

This theorized inhibition of gut metabolism of the target agent might have little or no effect in increasing systemic blood levels when the target agent is administered intravenously. Moreover, since the primary effect of the oral absorption enhancing agent may be a local effect in the gut lumen, doses which are subtherapeutic (e.g., in terms of immunosuppression) should be effective in achieving the desired effect. This is an important consideration in the case of enhancing agents such as cyclosporins which have powerful immunosuppressant activity and can present toxicity problems if administered at high dose levels. Our observation that non-immunosuppressive cyclosporins, such as cyclosporin F, can still function as an oral enhancer is of great clinical value.

It is important to note that while we provide hypotheses as to the mechanisms of action which underlie our invention, we do not actually know the mechanism(s) responsible for the surprising findings discussed herein; and this does not impede one of skill in the art from practicing the invention described. It may well be that none of the suggested mechanisms, some of them, or all of them play a part in the experimentally and clinically verified enhancement of taxane (specifically paclitaxel) oral bioavailability.

The dosage range of the enhancing agent to be co-administered with the target agent in accordance with the invention is about 0.1 to about 20 mg/kg of patient body weight. "Co-administration" of the enhancing agent comprehends administration substantially simultaneously with the target agent (either less than 0.5 hr. before, less than 0.5 hr. after or together), from about 0.5 to about 72 hr. before the administration of the target agent, or both, i.e., with one or more doses of the same or different enhancing agents given at least 0.5 hr. before and one dose given substantially simultaneously with (either together with or immediately before of after) the target agent. Additionally, "co-administration" comprehends administering more than one dose of target agent within 72 hr. after a dose of enhancing agent, in other words, the enhancing agent(s) need not be administered again before or with every administration of target agent, but may be administered intermittently during the course of treatment.

The dosage range of orally administered taxane target agents will vary from compound to compound based on its therapeutic index, the requirements of the condition being treated, the status of the subject and so forth. The method of the invention makes it possible to administer paclitaxel and other taxanes orally ranging from about 20 mg/m$^2$ to about 1000 mg/m$^2$ (based on patient body surface area) or about 2–30 mg/kg (based on patient body weight) as single or divided (2–3) daily doses, and maintain the plasma levels of paclitaxel in humans in the range of 50–500 ng/ml for extended periods of time (e.g., 8–12 hours) after each oral dose. These levels are at least comparable to those achieved with 96-hour IV infusion taxol therapy (which causes the patient great inconvenience, discomfort, loss of quality time, infection potential, etc.). Moreover, such plasma levels of paclitaxel are more than sufficient to provide the desired pharmacological activities of the target drug, e.g., inhibition of tubulin disassembly (which occurs at levels of about 0.1 $\mu$M, or about 85 ng/ml) and inhibition of protein isoprenylation (which occurs at levels of about 0.03 $\mu$M, or about 25 ng/ml) which are directly related to its antitumor effects by inhibiting oncogene functions and other signal-transducing proteins that play a pivotal role in cell growth regulation.

Preferred oral dosage amounts for paclitaxel and other taxanes administered according to the invention are about 50–200 mg/m$^2$ or about 2–6 mg/kg.

It may be suitable in some instances to administer to the patient a higher initial loading dose of the target agent to achieve peak blood levels, followed by lower maintenance doses.

Two or more different enhancing agents and/or two or more different target agents may be administered together, alternately or intermittently in all of the various aspects of the method of the invention.

The present invention also comprehends methods of treating human patients afflicted with cancers, tumors, Kaposi's sarcoma, malignancies, uncontrolled tissue or cellular proliferation secondary to tissue injury, and any other disease conditions responsive to paclitaxel, taxanes, docetaxel, and/or prodrugs and derivatives of all the foregoing such as paclitaxel 2'-MPM, and docetaxel 2'-MPM, with orally administered dosage forms comprising one or more of those agents. Among the types of carcinoma which may be treated particularly effectively with oral paclitaxel, docetaxel, other taxanes, and their prodrugs and derivatives, are hepatocellular carcinoma and liver metastases, cancers of the gastrointestinal tract, pancreas, prostate and lung, and Kaposi's sarcoma. Examples of non-cancerous disease conditions which may be effectively treated with these active agents administered orally in accordance with the present invention are uncontrolled tissue or cellular proliferation secondary to tissue injury, polycystic kidney disease, inflammatory diseases (e.g., arthritis) and malaria, including chloroquine- and pyrimethamine-resistant malaria parasites (Pouvelle et al.,*J. Clin. Invest.*, 44: 413–417, 1994).

The antitumor agents which heretofore were administered to human patients only parenterally can now be administered to humans in accordance with the invention by the oral route with sufficient bioavailability to provide pharmacologically active blood concentrations which will be particularly effective in the treatment of patients with primary tumors and metastases. The active ingredients will penetrate the gut wall as a result of the prior and/or concomitant administration of the cyclosporin enhancers and will be taken up by the portal circulation rapidly, providing a higher local initial concentration of the chemotherapeutic agents in the liver (a higher local concentration than is currently achieved with IV infusion therapy) than in the general systemic circulation or in most other organs at one and seven days. Furthermore, it should be noted that the higher levels of paclitaxel in the liver after oral administration may not be reflected in increased plasma levels because of the high first pass effect of the liver. The method of the invention, in selectively producing high blood concentrations of antitumor agents, is particularly valuable in the treatment of liver cancers (e.g., hepatocellular carcinoma and liver metastases), gastrointestinal cancers (e.g., colon, rectal) and lung cancers.

The plasma levels of the active target agents administered orally with the appropriate enhancing agents as provided in the present invention are remarkably and surprisingly similar to that observed upon IV administration. A series of studies with experimental animals showed that steady state plasma levels of paclitaxel were achieved upon oral co-administration with CsA by the third day of the regimen. The levels of the target agent achieved at steady state were comparable to those achieved in patients by a 96-hour IV infusion of paclitaxel. A 27% response rate was found in taxane-failure patients with metastatic breast cancer treated with a continuous 96-hour infusion every three weeks (Seidman et al., *J. Clin. Oncol.*, 14:1877, 1996). It is believed that similar results can be achieved with the treatment methods of the present invention, without the discomfort, inconvenience and risks of prolonged IV infusions.

The data reflected in FIGS. 1–4 are especially noteworthy and surprising. As described in more detail in the Examples set forth below, the data reflected in FIG. 1 were generated from studies of paclitaxel administration to rats, but the data reflected in FIGS. 2 and 3 reflect actual concentration levels of paclitaxel over time in the plasma of two human patients administered oral paclitaxel in accordance with the present invention, i.e., with co-administration of an oral cyclosporin enhancing agent. The human data are remarkable not merely because they reflect for the first time, to the extent found in the literature, that paclitaxel was administered orally to human beings requiring paclitaxel therapy, but also because therapeutic-level plasma concentrations were achieved and maintained over about a 24-hour period; indeed, the levels of drug seen in the plasma of the human patients were comparable to the levels achieved upon IV administration and the methods used did not bring about serious local or systemic side effects.

Apart from the animal (rat) test data reported in the Examples hereinafter and reflected in FIGS. 1 and 4, we conducted an extensive series of studies in rats wherein paclitaxel and other taxanes were administered orally together with cyclosporin A and other bioavailability enhancing cyclosporins C, D, F and G, and the results of these studies were reported and illustrated in co-pending parent application Ser. No. 08/733,142. Moreover, the effects of the oral administration of taxanes, particularly paclitaxel, to animal subjects concomitantly with oral doses of cyclosporins was compared in the parent application with the administration of the same target agents alone, by IV and oral routes, and the administration of other potential but less effective bioavailability enhancing agents together with the target drugs. The disclosures and experimental examples of application Ser. No. 08/733,142 are incorporated herein by reference.

It has now been demonstrated that the rat pharmacokinetic profile of paclitaxel co-administered with oral cyclosporin A is quite comparable to the profile in human patients receiving the same regimen. Indeed, FIG. 4 reflects a superimposition on the same graph of the plasma concentration curves for paclitaxel over a 24-hour period following oral co-administration of two doses of enhancer (cyclosporin A) spaced one hour apart with oral paclitaxel administered after the second dose of enhancer, said data being derived from the 24-hour rat study reflected in FIG. 1 and the studies on human patients reflected in FIGS. 2 and 3. It may be observed that the three curves on the graph in FIG. 4 (one rat and two human) are of very similar configuration, indicating that the results in humans are confirmatory of the animal test results.

The current application does not diminish or detract from the importance and relevance of data obtained in the rat. The rat is an accepted model for assessing the pharmacokinetics and absorption profiles of chemotherapeutic agents. However, because of known species-to-species variations, no clinician or medical practitioner could administer paclitaxel or other taxanes orally to humans with confidence based on the animal data alone without any human clinical experience. We have, contrary to conventional wisdom in the art, taught and actually provided a method whereby taxanes can be orally administered safely and effectively to humans. From the standpoint of a physician, the current invention is a vast improvement over the prior art, and teaches that the pharmacologic properties of a taxane such as paclitaxel can be utilized in clinical practice without the requirement for intravenous catheters and time spent in a hospital or chemotherapy clinic, without the attendant expense, inconvenience and risk of infection to the patient, and even without pre-medication to avoid hypersensitivity or allergic reactions, and potential adverse effects from the pre-medications themselves.

Oral dosage forms of the target agents whose bioavailability is increased by the co-administration of the enhancing agents may be in the form of conventional tablets, capsules (softgel or hard gel), caplets, gelcaps, pills, liquids (e.g., solutions, suspensions or elixirs), powders, lozenges, micronized particles or osmotic delivery systems and any other oral dosage forms known in the pharmaceutical arts. The liquid preparations may include, for example, paclitaxel or other taxane in a vehicle comprising CREMOPHOR EL or other polyethoxylated castor oil, alcohol and/or a polyoxyethylated sorbitan mono-oleate (e.g., TWEEN® 80, ICI Americas, Inc.) with or without flavoring. Each dosage form includes an effective amount of a taxane target agent and pharmaceutically inert ingredients, e.g., conventional excipients, vehicles, fillers, binders, disentegrants, solvents, solubilizing agents, sweeteners, coloring agents and any other inactive ingredients which are regularly included in pharmaceutical dosage forms for oral administration. Many such dosage forms and oral vehicles immediately after listings of inactive ingredients therefor are set forth in *Remington's Pharmaceutical Sciences,* 17th edition (1985).

Precise amounts of each of the target drugs in the oral dosage forms will vary depending on the age, weight, disease and condition of the patient. For example, paclitaxel or other taxane dosage forms may contain sufficient quantities of the target agent to provide a daily dosage of about 20–1000 mg/m$^2$ (based on patient body surface area) or about 2–30 mg/kg. mg/kg (based on patient body weight) as single or divided (2–3) daily doses. Preferred dosage amounts are about 50–200 mg/m$^2$ or about 2–6 mg/kg.

Dosing schedules for the treatment method of the present invention, for example, the treatment of paclitaxel-responsive diseases with oral paclitaxel dosage forms co-administered with enhancing agents, can likewise be adjusted to account for the patient's characteristics and disease status. Preferred dosing schedules for administration of oral paclitaxel are (a) the daily administration to a patient in need thereof of 1–3 equally divided doses providing about 20–1000 mg/m$^2$ (based on body surface area), and preferably about 50–200 mg/m$^2$, with said daily administration being continued for 1–4 consecutive days each 2–3 weeks, or (b) administration for about one day each week. The former schedule is comparable to use of a 96-hour paclitaxel infusion every 2–3 weeks, which is considered by some a preferred IV treatment regimen.

Oral administration of taxanes in accordance with the invention may actually decrease toxic side effects in many cases as compared with currently utilized IV therapy. Rather than producing a sudden and rapid high concentration in blood levels as is usually the case with an IV infusion, absorption of the active agent through the gut wall (promoted by the enhancing agents), provides a more gradual appearance in the blood levels and a stable, steady-state maintenance of those levels at or close to the ideal range for a long period of time.

Pursuant to another aspect of the invention, combination oral dosage forms are provided which contain fixed quantities of at least one enhancing agent and at least one target agent. For example, such dosage forms can consist of tablets, capsules, caplets, gelcaps, pills, liquids, lozenges and any other conventional oral dosage forms containing as active ingredients an effective oral bioavailability enhancing amount of an antitumor or anti-neoplastic agent, as well as suitable inactive ingredients. One such combination product includes from about 0.1 to about 20 mg/kg of one or more of cyclosporins A, D, C, F and G, dihydro CsA, dihydro CsC and acetyl CsA together with about 20 to about 1000 mg/m$^2$ (based on average patient body surface area), and preferably about 50–200 mg/m$^2$, of paclitaxel, docetaxel, other taxanes or paclitaxel or docetaxel derivatives such as paclitaxel 2'-MPM or docetaxel 2'-MPM.

The co-administration of enhancing agents with the target drugs promotes not only the oral bioavailability of those agents but also enables their use in the treatment of tumors at sites highly protected by MDR, e.g., the testes and the brain. Another aspect of the present invention is, thus, a method of delivering antitumor drugs to tumor sites protected by MDR through the oral co-administration of enhancing agents and the antitumor agents, making it possible to treat brain tumors such as glioblastoma multiforme.

Further advantages of the present invention are in the area of safety. Because of its physico-chemical properties, paclitaxel must be solubilized in a Cremophor/ethanol mixture and that vehicle may be responsible for at least some of the allergic-type reactions experienced by patients on paclitaxel therapy. Other solubilizing agents have been used but none have been as suitable as Cremophor/ethanol. Paclitaxel must be given slowly to patients, with medical personnel in a state of constant vigilance for severe hypersensitivity reactions. For standard intravenous regimens, pre-medication regimens of H-1 and H-2 blockers plus steroids are generally required. However, even when Cremophor/ethanol solubilization is not used, intravenous taxanes can still bring about severe reactions following intravenous use. Thus, docetaxel administration is associated with anasarca and other reactions. Therapies with the potential to eliminate or diminish the need for pre-medication in these settings would be very valuable clinically.

The present invention, in one of its embodiments, provides a method of preventing or reducing hypersensitivity and allergic reactions in human patients receiving taxane therapy. The method comprises the oral administration of the taxane to the patients. Oral administration by the instantly disclosed method is much less likely than intravenous therapy to produce such adverse reactions. Indeed, we administered paclitaxel to human patients (see Examples 2 and 3) with no pre-medication (i.e., with H-1 or H-2 blockers or steroids), and no hypersensitivity reactions were observed while achieving therapeutic circulating levels.

Furthermore, paclitaxel use is associated with a variety of toxicities and side-effects. Two of the most noteworthy toxicities are neutropenia and neuropathy. A variety of clinical data have shown that it would be desirable to keep the circulating plasma concentrations within a certain "window" in order to maximize the anti-tumor activity and minimize the side effects, especially neutropenia. For many tumor types, it is believed that low, but long-term, exposure of tumor cells in the body results in better clinical results. Thus, plasma levels of about 0.03 micromolar would be expected to inhibit cancer-cell protein isoprenylation and levels of about 0.1 micromolar would be expected to block disassembly of microtubules. There are clinical data showing that constant intravenous administration over several days to achieve a "window" of about 0.05 to 0.1 micromolar in the circulation can minimize toxicities and cause tumor regressions, sometimes even in patients whose tumors did not respond to 3-hour infusion regimens. The currently approved 3-hour infusion regimens of paclitaxel achieve peak plasma concentrations that greatly exceed these levels The present invention also makes it possible to give paclitaxel in comparatively infrequent daily doses (e.g., about twice/day) and according to schedules that would otherwise not be possible or practical with the intravenous route. The use of the enhancer (e.g., cyclosporin A) promotes oral absorption of paclitaxel for the first dose and if a second paclitaxel dose is to be given later in the day, the use of additional cyclosporin A may not even be needed. Thus, paclitaxel could be given intermittently as single dose on a fixed schedule (weekly, biweekly, etc.) or chronically, over a period of consecutive days (e.g., 4 days) every 2–4 weeks with the goal of keeping the levels within a safe and effective "window".

The following examples illustrate various aspects of the invention and demonstrate the unexpected, very substantial increases in the oral absorption of paclitaxel achieved. These examples are not intended, however, to limit the invention in any way or to set forth specific enhancing or target agents, dosage ranges, testing procedures or other parameters which must be used exclusively to practice the invention.

EXAMPLE 1

Six (6) healthy Sprague Dawley rats, all weighing from 225–275 grams and approximately six to eight weeks old, received a single oral dose of paclitaxel at 9 mg/kg. Blood samples were collected from the tail vein of each rat at 0.5, 1, 2, 3, 4 and 6 hours after the paclitaxel dose. The individual samples were centrifuged and the serum was separated. For each time interval, the six samples were composited to produce a single representative sample. All samples were assayed for unchanged paclitaxel by LC/MS with a lower limit of quantitation of 50 pg/ml.

The results of the study are graphically illustrated in the lower curve of FIG. 1, which indicates that the bioavailability of the orally administered paclitaxel in serum was less than 1%.

EXAMPLE 2

Ten (10) healthy Sprague Dawley rats with the same characteristics as those used in the study described in Example 1 were treated with 5 mg/kg of oral cyclosporin A followed 1 hour later with another 5 mg/kg dose of oral cyclosporin A and 9 mg/kg of oral paclitaxel.

Blood samples were collected from the tail vein of each rat at 0.25, 0.5, 1, 2, 3, 4, 5, 6, 8, 12 and 24 hours after paclitaxel administration. After appropriate treatment of the samples and the creation of one composite sample for the group, the plasma from each sample was assayed for unchanged paclitaxel.

The results of this study are graphically illustrated in the upper curve of FIG. 1. It may be observed that the plasma levels of paclitaxel in this group of animals was several times higher during the first six hours than in the rats of Example 1 who received paclitaxel alone, that levels at or above the "target" therapeutic levels were maintained for (8) eight hours after dosing and that significant plasma levels were maintained throughout the 24-hour period.

EXAMPLE 3

A 71-year old man with prostate cancer for three years agreed to receive an oral dose of paclitaxel and an enhancer in the form of cyclosporin A. His body surface area was 2.04 square meters and his weight was approximately 84 kilograms. After an overnight fast, he received two oral doses of cyclosporin A (Sandimmune 5 mg/kg) one hour apart. Just after the second dose, the patient drank a Cremophor/alcohol-based solution-dose of paclitaxel containing 180 mg dissolved in 120 ml of 5% dextrose in water, i.e., about 2.0 mg/kg of body weight or about 90 mg/m² of body area. Standard premedications, as one would use for short term infusions of taxanes, were not given. After drinking the solution, the patient remarked that the taste was unpleasant. He experienced some loose stools for a few hours. He also reported some flushing several hours after dosing which may have been related to the temporary cessation of his antihypertensive medication. His clinical course was otherwise unremarkable.

Figure 2:
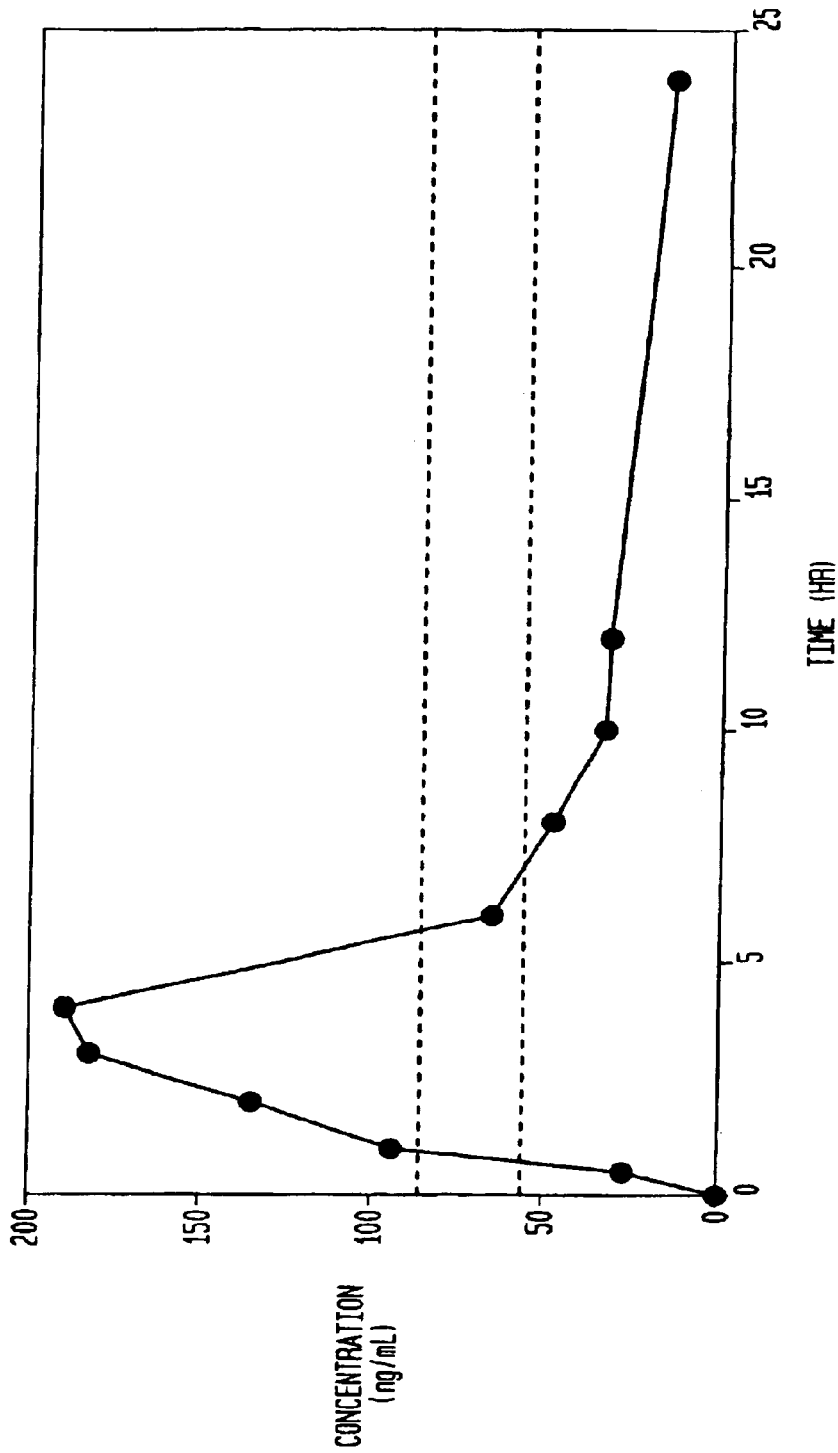
FIG. 2 is a graph reflecting the levels of paclitaxel in plasma samples from a human patient administered oral paclitaxel after two doses of oral cyclosporin A, the first administered one hour before the paclitaxel dose and the second administered immediately before the paclitaxel.

Plasma samples were obtained at frequent intervals following the administration of paclitaxel and were assayed by LC/MS/MS. The plasma level results over time are shown in FIG. 2. Peak was reached about 4 hours post dosing and levels above 0.07 micromolar were achieved from about one to five hours. Levels comparable to those found in breast cancer patients receiving 96-hour intravenous infusions of paclitaxel (0.05 micromolar) were present for about 10–12 hours (Seidman et al., *J. Clin. Oncol.*, 14:1877, 1996).

EXAMPLE 4

A 75-year old man with prostate cancer for several years received an oral dose of paclitaxel and cyclosporin A. His body surface area was 1.82 square meters and his weight was approximately 72 kilograms. After an overnight fast, he received the same regimen of cyclosporin A (Sandimmune 5 mg/kg) and oral paclitaxel (180 mg) as the patient in Example 1, which equaled about 2.5 mg/kg or about 100 mg/m² of paclitaxel in this patient. Again, standard premedications, as one would use for short-term infusions of taxanes, were not given. After drinking the solution, the patient remarked that the taste was unpleasant. He experienced some loose stools for a few hours. He also had a modest decline in blood pressure after dosing which may have been related to a vasovagal reaction secondary to his fasting state and blood draws. As a precaution the patient received about 100 ml of saline intravenously. After eating lunch he felt much better and the remainder of his clinical course was otherwise unremarkable.

Figure 3:
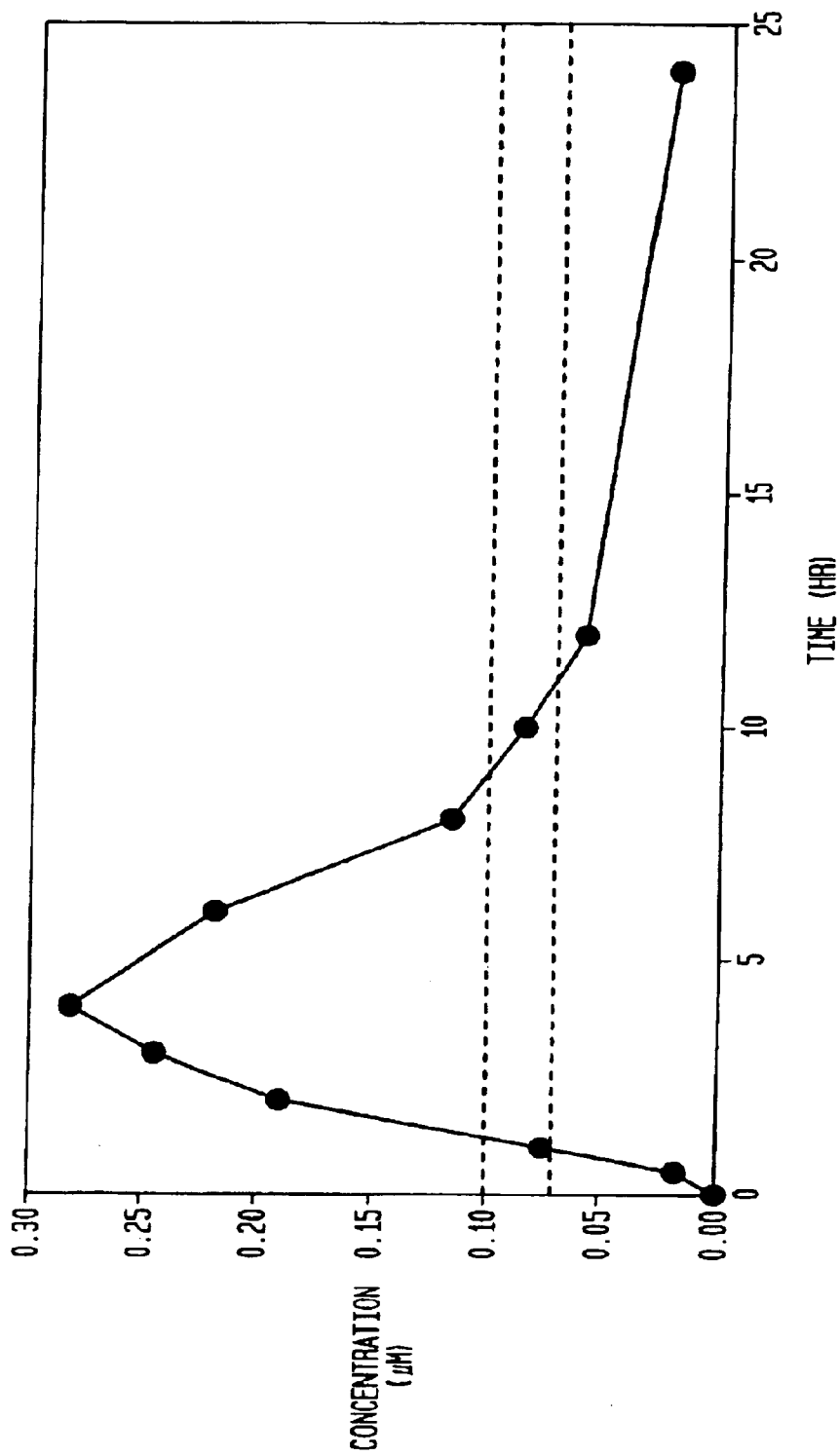
FIG. 3 is graph reflecting the levels of paclitaxel in plasma samples from a second human patient administered oral paclitaxel by the same regimen as described with respect to FIG. 2.

Plasma samples were obtained at frequent intervals following the administration of paclitaxel and were assayed by LC/MS/MS. The plasma level results over time are shown in FIG. 3. The peak level was almost 0.3 micromolar and occurred at 4 hours post dosing. Levels above 0.07 micromolar were achieved from about one to ten hours. Levels comparable to those found in breast cancer patients receiving 96-hour intravenous infusions of paclitaxel were present for about 12–15 hours.

As noted previously, FIG. 4 represents a composite of the paclitaxel concentration levels determined over time in rats (upper curve from FIG. 1) and in humans (curves from FIGS. 2 and 3) administered oral paclitaxel following two doses of oral cyclosporin spaced one hour apart, in accordance with the present invention. It will be observed that the concentration levels achieved in humans not merely confirm the efficacy of the present invention in making paclitaxel orally bioavailable for the first time, but they exceed the concentration levels achieved in the rat model. These results are unexpected and surprising and, until we demonstrated the clinical efficacy of the subject method in human beings, it could not have been predicted based on any prior art disclosures regarding cyclosporins or other potential enhancing agents or regarding paclitaxel, its derivatives, analogs and prodrugs or other taxanes.

It has thus been shown that there are provided methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed is:

1. A method of preventing or reducing hypersensitivity or allergic reactions in a human patient undergoing taxane therapy for a taxane-responsive disease condition, comprising orally co-administering to the patient a taxane and an oral bioavailability enhancing agent comprising an inhibitor of P-glycoprotein, without prior administration of medication to prevent the hypersensitivity or allergic reactions, wherein the taxane reaches therapeutic blood or plasma levels in said patient.

2. The method of claim 1, wherein the taxane is selected from the group consisting of paclitaxel and analogs, derivatives and prodrugs thereof.

3. The method of claim 1 wherein the taxane is a analog of paclitaxel.

4. The method of claim 3, wherein the analog of paclitaxel is docetaxel.

5. The method of claim 1, wherein the enhancing agent is administered either a) about 0.5–72 hrs. before, b) less than 0.5 hr. before, together with or less than 0.5 hr. after, or c) both about 0.5–72 hrs. before and again less than 0.5 hr. before, together with or less than 0.5 hr. after, the administration of the taxane.

6. The method of claim 1, wherein the taxane and the enhancing agent are administered in separate oral dosage forms.

7. The method of claim 1, wherein the taxane and the enhancing agent are administered together in a combination oral dosage form.

8. The method of claim 1, wherein the taxane is paclitaxel.

9. The method of claim 1, wherein the enhancing agent is administered in an amount of from about 0.1 to 20 mg/kg of patient body weight.

10. The method of claim 8, wherein the paclitaxel and the enhancing agent are orally co-administered once a week.

11. The method of claim 10, wherein the paclitaxel is administered in a divided dose.

12. The method of claim 5, wherein the taxane is docetaxel.

13. The method of claim 1, wherein two or more doses of the taxane are administered after a single dose of the enhancing agent.

14. The method of claim 1, wherein the patient is administered about 20–1,000 mg/m² of the taxane based on patient body surface area.

15. The method of claim 14, wherein the patient is administered about 50–200 mg/m² of the taxane based on patient body weight.

16. The method of claim 1, wherein the patient is administered about 2–30 mg/kg of paclitaxel based on patient body weight.

17. The method of claim 16, wherein the patient is administered about 2–6 mg/kg of paclitaxel.

18. The method of claim 1, wherein the taxane, the enhancing agent or both is each administered in a dosage form selected from the group consisting of tablets, softgel capsules, hardgel capsules, caplets, gelcaps, pills, lozenges, powders, micronized particles, osmotic delivery systems, and liquid solutions, suspensions and elixirs.

19. The method of claim 8, wherein paclitaxel is administered in a formulation further comprising a polyethoxylated castor oil, alcohol or polyoxyethylated sorbitan monooleate.

20. The method of claim 1, wherein the disease condition is a cancer, tumor, malignancy, uncontrolled tissue or cellular proliferation secondary to tissue injury, or an inflammatory disease.

21. The method of claim 1, wherein the disease condition is selected from the group consisting of gastrointestinal tract cancers, lung cancers, pancreatic cancer, prostate cancer, hepatocellular carcinoma, liver metastases, genito-urinary and gastrointestinal tract cancers, Kaposi's sarcoma, polycystic kidney disease and malaria.

22. The method of claim 1, wherein the disease condition is cancer.

23. The method of claim 22, wherein the taxane is paclitaxel.

24. The method of claim 23, wherein the patient is administered about 50–200 mg/m$^2$ of paclitaxel based on patient body weight.

25. The method of claim 24, wherein paclitaxel and the enhancing agent are orally co-administered about once per week.

26. The method of claim 25, wherein paclitaxel is administered in a divided dose.

27. The method of claim 1, wherein the taxane is docetaxel.

28. The method of claim 1, wherein the disease condition is lung cancer.

29. The method of claim 28, wherein the taxane is paclitaxel.

30. The method of claim 29, wherein the patient is administered about 50–200 mg/m$^2$ of paclitaxel based on patient body weight.

31. The method of claim 30, wherein paclitaxel and the enhancing agent are orally co-administered about once per week.

32. The method of claim 31, wherein paclitaxel is administered in a divided dose.

33. The method of claim 28, wherein the taxane is docetaxel.

34. The method of claim 33, wherein from about 0.1 to about 20 mg/kg of the enhancing agent are orally administered to the patient.

35. The method of claim 1, wherein the disease condition is a cancer of the gastrointestinal tract.

36. The method of claim 35, wherein the taxane is paclitaxel.

37. The method of claim 36, wherein the patient is administered about 50–200 mg/m$^2$ of paclitaxel based on patient body weight.

38. The method of claim 37, wherein paclitaxel and the enhancing agent are orally co-administered about once per week.

39. The method of claim 38, wherein paclitaxel is administered in a divided dose.

40. The method of claim 35, wherein the taxane is docetaxel.

41. The method of claim 40, wherein from about 0.1 to about 20 mg/kg of the enhancing agent are orally administered to the patient.

42. The method of claim 1, wherein the disease condition is ovarian cancer.

43. The method of claim 42, wherein the taxane is paclitaxel.

44. The method of claim 43, wherein the patient is administered about 50–200 mg/m$^2$ of paclitaxel based on patient body weight.

45. The method of claim 44, wherein paclitaxel and the enhancing agent are orally co-administered about once per week.

46. The method of claim 45, wherein paclitaxel is administered in a divided dose.

47. The method of claim 3, wherein the taxane is docetaxel.

48. The method of claim 47, wherein from about 0.1 to about 20 mg/kg of the enhancing agent are orally administered to the patient.

49. The method of claim 1, wherein the disease condition is breast cancer.

50. The method of claim 49, wherein the taxane is paclitaxel.

51. The method of claim 50, wherein the patient is administered about 50–200 mg/m$^2$ of paclitaxel based on patient body weight.

52. The method of claim 51, wherein paclitaxel and the enhancing agent are orally co-administered about once per week.

53. The method of claim 52, wherein paclitaxel is administered in a divided dose.

54. The method of claim 49, wherein the taxane is docetaxel.

55. The method of claim 54, wherein from about 0.1 to about 20 mg/kg of the enhancing agent are orally administered to the patient.

* * * * *